United States Patent [19]

Earnshaw et al.

[11] Patent Number: 5,070,192
[45] Date of Patent: Dec. 3, 1991

[54] CLONED HUMAN TOPOISOMERASE I: CDNA EXPRESSION, AND USE FOR AUTOANTIBODY DETECTION

[75] Inventors: William C. Earnshaw, Monkton; Peter D'Arpa, Baltimore, both of Md.

[73] Assignee: The Johns Hopkins University, Baltimore, Md.

[21] Appl. No.: 172,159

[22] Filed: Mar. 23, 1988

[51] Int. Cl.$^5$ .................. C07H 21/04; C12Q 1/68; G01N 33/532; G01N 33/564

[52] U.S. Cl. .................. 536/27; 435/7.1; 435/91; 435/172.3; 436/501; 436/543; 436/536; 436/811; 436/815; 530/387; 935/12; 935/14; 935/29; 935/36; 935/81; 935/88

[58] Field of Search .................. 435/7, 91, 172.3; 436/501, 543, 536, 811, 815; 530/387; 536/27; 935/12, 14, 29, 36, 81, 88

[56] References Cited

PUBLICATIONS

Juarez et al. (1988), Arthritis and Rheumatism, vol. 31, No. 1, pp. 108–115.
Douvas, et al. (1979), Journal of Biological Chemistry, 254:10514–10522.
Liu, et al. (1981), Proc. Nat. Acad. Sci., 78:3487–3491.
McConaughy, et al. (1981), Biochim, Biophys. Acta, 655:1–8.
Geisler, et al. (1985), Journal of Immunological Methods, 80:211–219.
Thrash, et al. (1985), Proc. Nat. Acad. Sci., 82:4374–4378.
Goto, et al. (1985), Proc. Nat. Acad. Sci., 82:7178–82.
Shero, et al. (1986), Science, 231:737–740.
Guldner, et al. (1986), Chromosoma, 94:132–138.
Maul, et al. (1986), Proc. Nat. Acad. Sci., 83:5145–5149.
Uemura, et al. (1987), Nucleic Acid Research, 15:9727–9739.
D'Arpa, et al. (1988), Proc. Nat. Acad. Sci., 85:2543–2547.
Samuels et al., "Inhibition of Topoisomerase I by Antibodies in Sera from Scleroderma Patients," FEBS 4289 (1986), 209:231–234.
Durban, et al., Biochemical and Biophysical Research Communication, 154:358–364 (1988).

Primary Examiner—Robert A. Wax
Assistant Examiner—Ardin H. Marschel
Attorney, Agent, or Firm—Banner, Birch, McKie & Beckett

[57] ABSTRACT

The invention relates to cDNA molecules coding for eukaryotic topoisomerase I polypeptide. The invention provides cDNA mlecules comprising a part of the cDNA sequence of topoisomerase I which encode at least one epitope for autoantibodies to eukaryotic topoisomerase I. The invention also provides cloning vehicles capable of replication and expression comprising cDNA molecules coding for eukaryotic topoisomerase I. The invention further provides for hosts transformed with a vehicle having a cDNA molecule coding for eukaryotic topoisomerase I. In another embodiment, the invention provides for the detection of autoantibodies to eukaryotic topoisomerase I using the eukaryotic topoisomerase I polypeptides coded for by the cDNA molecules of the invention.

16 Claims, 7 Drawing Sheets

```
                                                                              GAATTCGGCACGAGGGCCCCCCCCAGTCAGGCTACGACCGTGCCCCTCGCCCCGTTTCTCGAGTCTCCGCCCAC
AGTCACCGCGGCTTACCTGGCCCCTCGAGCCTCCGAGCCTCGAGCCTCGGTCCGCACACGCCCCGGTTCGCGGTCGCTGCCCTCCCCCGAGCCTCCCCCCGGTTCCCCCGAGCCTCCCCCGACC    32
ATG AGT GGG GAC CTC CAC AAC GAT TTC CGA ATC CAG CCG GAT TTG AAT GAT TCT CAT AAA CAC AAA GAT CGA GAA
MET Ser Gly Asp Leu His Asn Asp Phe Arg Ile Gln Pro Asp Leu Asn Asp Ser His Lys Asp Lys Asp Arg Glu     64
 33
CAC CAC AAA GAA AAG GAG AAG GAC CGG GAA AAG TCC AAC AAG GAA CAT AAA AGT GAA CAT AAA AAG AAA GAG AAG
His His Lys Glu His Glu Lys Asp Arg Glu Lys Ser Asn Lys Glu His Lys Ser Glu His Lys Lys Lys Glu Lys     96
 65
GAG AAG ACC AAA GAT GGA AGC TCA GAA AAA CAT AAA GAC AGA GAC AAG CCA AAA GAG GAA AAG GTT CGA GCC
Glu Lys Thr Lys His Lys Ser Gly Ser Ser Glu Lys His Lys Asp Arg Asp Lys Arg Lys Glu Glu Lys Val Arg Ala  128
 97
TCT GCG GAT GCA AAA ATA AAG GAG AAG GAA AAT GCC TTC TCT CCA CAA ATT GAT GAA CCT GAG GAT GGC TAT TTT GTT CCT
Ser Gly Asp Ala Lys Ile Lys Glu Lys Glu Asn Gly Phe Ser Pro Gln Ile Asp Glu Pro Glu Asp Gly Tyr Phe Val Pro  160
129
CCT AAA GAG GAT ATA AAG CCA CTA AAG AGA CCA GAT GAG GTT GAT GTT AAA CCC AAG AAT AAA GAT TAT CCT GAG CCA GAT AAC AAG
Pro Lys Glu Asp Ile Lys Pro Leu Lys Arg Pro Arg Asp Glu Val Asp Val Lys Pro Lys Asn Lys Asp Tyr Pro Glu Pro Asp Asn Lys  192
161
AAG AAA AGA GAA CTA GAA GAA GAG GAT GGT AAA TTG CTT CCA GAG CGC ATC AAC TGG AAA TTC TTA GAA CAT AAA GGT
Lys Lys Arg Glu Leu Glu Glu Glu Asp Gly Lys Leu Leu Pro Glu Arg Ile Asn Trp Lys Phe Leu Glu His Lys Gly  256
193
AAG AAG CCG AAG AAA GAG GAA GAG CAG CAG AAG TGG TGG AAA TCC AAG AGC TAT CCT GAA GAG CGC TAT CCT GGA GAA CAT CTA GAA CAT AAA GGT
Lys Lys Pro Lys Lys Glu Glu Glu Gln Gln Lys Trp Trp Trp Ile Ser Lys Ser Tyr Pro Glu Glu Arg Tyr Pro Gly Ile Glu Leu Glu His Lys Gly  256
225
CCA GTA TTT GCC CCA CCA TAT GAG CCT CTT CCA GAG AAT GTC ATG AAG TTT TAT GAT GGT AAA GTC ATG AAG CTG AGC CCC AAA GCA GAG GAA GTA
Pro Val Phe Ala Pro Pro Tyr Glu Pro Leu Pro Glu Asn Val MET Lys Phe Tyr Asp Gly Lys Val MET Lys Leu Ser Pro Lys Ala Glu Glu Val  288
257
GCT ACG TTC TTT GCA AAA ATG CTC GAC CAT GAA AAA ATC ACC AAG GAA ATA TTT AGG AAA GAA TGG AGA AAG GAA ATG ACT AAT
Ala Thr Phe Phe Ala Lys MET Leu Asp His Glu Lys Ile Thr Thr Lys Glu Ile Phe Arg Lys Glu Trp Arg Lys Glu MET Thr Asn  320
289
GAA GAG AAG AAT ATT ACC AAC CTA AGC AAA TGT GAT TTC ACC CAG ATG AGC CAG TTT GCC ATG ACG CGG GAA GCT CCG AAA CAG AGC
Glu Glu Lys Asn Ile Thr Asn Leu Ser Lys Cys Asp Phe Thr Gln MET Ser Gln Tyr Phe Lys Ala Gln Thr Glu Ala Arg Lys Gln MET Ser
```

FIG. 5B

```
321
AAG GAA GAG AAA ATC AAA GAG GAG AAT GAA AAA TTA CTC AAA GAA TAT GGA TTC TGT ATT ATG GAT AAC CAC AAA GAG AGG ATT GCT AAC
Lys Glu Glu Lys Ile Lys Glu Glu Asn Glu Lys Leu Leu Lys Glu Tyr Gly Phe Cys Ile MET Asp Asn His Lys Glu Arg Ile Ala Asn
353                                                                                                                  384
TTC AAG ATA GAG CCT CCT GGA CTT TTC CGT GGC GGC AAC CAC CCC AAG ATG ATG CGA ATC ATG CCC GAG GAT ATA ATC ATC
Phe Lys Ile Glu Pro Pro Gly Leu Phe Arg Gly Arg Gly Asn His Pro Lys MET MET Arg Ile MET Pro Glu Asp Ile Ile Ile
385                                                                                                          416
AAC TGT AGC AAA GAT GCC AAG GTT CCT CCT CCA GGA CAT AAG GTC CGG CAT AAC GTT AAG GTT ACT TGG CTG GTT TCC TGG
Asn Cys Ser Lys Asp Ala Lys Val Pro Pro Pro Gly His Lys Val Arg His Asn Val Lys Val Thr Trp Leu Val Ser Trp
417                                                                                                       448
ACA GAG AAC ATC CAA GGT TCC ATT AAA TAC ATC CTT AAC CCT AGT AGT CGA ATC AAG GGT GAG AAG GAC TGG CAG AAA TAC GAG ACT GCT CGG
Thr Glu Asn Ile Gln Gly Ser Ile Lys Tyr Ile Leu Asn Pro Ser Ser Arg Ile Lys Gly Glu Lys Asp Trp Gln Lys Tyr Glu Thr Ala Arg
449                                                                                                                          480
CGG CTG AAA AAA TGT GTG GAC AAG ATC CGG AAC CAG TAT CGA GAA GAG ATG AAA TCC AAA GAG ATG AAA GTC CGG CAG AGA GCT GTA GCC CTG TAC
Arg Leu Lys Lys Cys Val Asp Lys Ile Arg Asn Gln Tyr Arg Glu Glu MET Lys Ser Lys Glu MET Lys Val Arg Gln Arg Ala Val Ala Leu Tyr
481                                                                                                                              512
TTC ATC GAC AAG CTT GCT CTG AGA GCA GCC AAT GAA AAG GAG ACA GCG GAC ACT GTG GGC TGC TCA CTT CGT GTG GAG CAC ATC
Phe Ile Asp Lys Leu Ala Leu Arg Ala Ala Asn Glu Lys Glu Thr Ala Asp Thr Val Gly Cys Ser Leu Arg Val Glu His Ile
513                                                                                                          544
AAT CTA CAC CCA GAG TTG GAT GGT CAG GAA TAT GTG GTA TTT GAC CAG GAG TTC TTC GGG AAG GAC TCC ATC AGA TAC TAT AAC AAG GTC CCT GTT GAG
Asn Leu His Pro Glu Leu Asp Gly Gln Glu Tyr Val Val Phe Asp Gln Glu Phe Phe Gly Lys Asp Ser Ile Arg Tyr Tyr Asn Lys Val Pro Val Glu
545                                                                                                                                    576
AAA CGA GTT TTT AAG AAC CTA CAA CTA ATG GAG AAC AAG CAG CCC GAG GAT CTT TTT GAT AGA CTT ATT ACT AAT CTC AAT AAG CAT
Lys Arg Val Phe Lys Asn Leu Gln Leu MET Glu Asn Lys Gln Pro Glu Asp Leu Phe Asp Arg Leu Ile Thr Gly Leu Asn Lys His
```

FIG. 5C

```
577
CTT CAG GAT CTC ATG GAG GGC TTG ACA GCC AAG GTA TTC CGT ACG TAC AAT GCC TCC ATC ACG CAG CAG CTA AAA GAA CTG ACA GCC CCG
Leu Gln Asp Leu MET Glu Gly Leu Thr Ala Lys Val Phe Arg Thr Tyr Asn Ala Ser Ile Thr Gln Gln Leu Lys Glu Leu Thr Ala Pro
609                                                                                                                    640

GAT GAG AAC ATC CCA GCG AAG ATC CTT TCT TAT AAC CGT GCC AAT CGA GCT GTT GCA ATT CTT TGT AAC CAT CAG CGA ATT CAG CCA AAA ACT TTT
Asp Glu Asn Ile Pro Ala Lys Ile Leu Ser Tyr Asn Arg Ala Asn Arg Ala Val Ala Ile Leu Cys Asn His Gln Arg Ala Pro Lys Thr Phe
641                                                                                                                    672

GAG AAG TCT ATG ATG AAC TTG CAA ACT TAG ATT GAT GCC CGG AGA GAC CTG AAA AGT GCT AAG GCT GAT GCC
Glu Lys Ser MET MET Asn Leu Gln Thr Lys Ile Asp Ala Asp Ala Arg Arg Asp Leu Lys Ser Ala Lys Ala Asp Ala
673                                                                                                    704

AAG GTC ATG AAG GAT GCA AAG ACG AAG AAG GTA TCA AAG AAG AAG GCT GTT CAG AGA CTG GAG GAA CAG TTG ATG AAG CTG GAA GTT CAA
Lys Val MET Lys Asp Ala Lys Thr Lys Lys Val Ser Lys Lys Lys Ala Val Gln Arg Leu Glu Glu Gln Leu MET Lys Leu Glu Val Gln
705                                                                                                                    736

GCC ACA GAC CGA GAA AAT AAA CAG ATT GCC CTG GGA ACC TCC AAT CTC AAT TAT CTG GAC CCT ACG ATC ACA GTG GCT TGG TGC AAG AAG TGG
Ala Thr Asp Arg Glu Glu Asn Lys Gln Ile Ala Leu Gly Thr Ser Leu Asn Tyr Leu Asp Pro Arg Ile Thr Val Ala Trp Cys Lys Lys Trp
737                                                                                                                    765

GGT GTC CCA ATT GAG AAG ATT TAC AAC AAA ACC CAG AAG TTT GCC ATT GAC GCT GAA GAC TAT GAG TTT TAG CCAGTCT
Gly Val Pro Ile Glu Lys Ile Tyr Asn Lys Thr Gln Lys Phe Ala Ile Asp Ala Glu Asp Tyr Glu Phe *

CAAGCCCAGAGTTCTGAGATTATAACGAGGAACAGTGTGGTTTGGAAAGATGAATAAACTGAGCCTACTTGCCCTTGGTGCCTTGCGTGCCAAAG
CAGACCTGACATATTATAACGGAGACTGACCAGTCTGTCCAGGCACCACAAGCACCAAGTCTAAGAACCACCAACCATCTTTCCGAAAG
ATAAACCTGGAGATATGGAATTTGTCACGCAGCTCATCAGTTGCATTCCTGATGATGCCTATCTAGCTCCTGATCAAAATTCTACTCTGTATGTT
GCCAAGTGGATGGAATTTAATAGAAATAATTCATGAATTTAAAATTTGCATCTCTGAAGTTGTTTGCATTCAGAAACAACACTGTTCAGAACATGATGTCCAAAATATTCCGACTTGAGTGTACTCTATTGT
CCATAACTTACTCAATCAATTAACTGAAGCAGTGTGGTCCTTTGCAGTTTGGTTCAACCACCTGTAGATTGGTGTAGATTGCTTGAGTGCTTAGGGTTTT
CATCTGGATCAATTCATTAATTAACCTTTTCTTAAATATTTAACCTTTTATCCCTGTAACCTAAGATATCCATCTTTCACTTAAAGATTTACTTTGAAGATTCCACTGTTAAAATGGCCCACCAAGATATTACAGTCAA
GAATTTTTTTTTTTCCATCATCCTTGTTCTGAGCATTGCTGAAAAAATGAATGAGTATGTGTCAAAAAAAAGGAAAATAATCACATTTGGCTTTATTTTGTAAATTGAAAAACATAAAGTTTCCAGTCAA
TGAAACATTTAGAGCAAATAGTAGATTATTTGTCAAAAAAAAAGGAAAATAATCACATTTGGCTTTATTTTGTAATTGTAAAACATAAAACATAAAGTTTCCAGTCAA
TAAACTTAGAGCAAAATTGTCGTAGCCATTAGTTTAGAGGCCATGTTAGTTTTAGGTGTGTGTCCAGAGTCCATTCCCACATCTTCTATTTATTATTTATCATGAATTC
CAAACATTTTTCCTATAATCATTAGTTTAGAGGCCATGTTAGTTTTAGGTGTGTGTCCAGAGTCCATTCCCACATCTTCTATTTATTATCATGAATTC
```

FIG. 6A

CLONED HUMAN TOPOISOMERASE I: CDNA EXPRESSION, AND USE FOR AUTOANTIBODY DETECTION

BACKGROUND OF THE INVENTION

This work was supported a Grant from the National Institutes of Health. The United States Government may retain certain rights in this invention.

FIELD OF THE INVENTION

The present invention relates to the use of recombinant DNA technology for the transformation of a host organism with eukaryotic genetic sequences for the expression of topoisomerase I polypeptides and methods of using topoisomerase I polypeptides to detect autoantibodies to topoisomerase I polypeptides.

DESCRIPTION OF THE BACKGROUND ART

DNA topoisomerases I and II catalyze the breaking and rejoining of DNA strands in a way that allows the strands to pass through one another, thus altering the topology of DNA. Type I topoisomerases break a single DNA strand, while the type II enzymes break two strands of duplex DNA. Both enzymes can perform a variety of similar topological interconversions, including relaxation of super coiled DNA, knotting/unknotting and catenation/decatenation of duplex DNA.

Both topoisomerases I and II can provide the topological interconversions necessary for transcription and replication. For example, topoisomerase I can provide the necessary unlinking activity for efficient in vitro DNA replication (Minden, et al., *Journal of Biological Chemistry*, 260:9316, 1985; Nagata, et al., *Proceedings of the National Academy of Sciences, U.S.A.*, 80:4266, 1983; Yang, et al., *Proceedings of the National Academy of Sciences, U.S.A.*, 84:950, 1987) however, topoisomerase II can also facilitate the replication of SV40 DNA by HeLa cell lysates (Yang, et al., *Proceedings of the National Academy of Sciences, U.S.A.*, 84:950, 1987). Genetic studies in yeast reveal that both replication and transcription proceed in single mutants deficient in either topoisomerase I or II (Goto, et al. *Proceedings of the National Academy of Sciences, U.S.A.*, 82:7178, 1985; Uemura, et al., *EMBO Journal*, 3:1737, 1984; Thrash, et al., *Proceedings of the National Academy of Sciences, U.S.A.*, 82:4374, 1985). In cells lacking both topoisomerases, transcription and replication are dramatically reduced (Uemura, et al., *EMBO Journal*, 5:1003, 1986; Brill, et al., *Nature*, 326:414, 1987).

Several lines of evidence suggest that topoisomerase I normally functions during transcription. The enzyme has been shown to be localized preferentially to actively transcribed loci by immunofluorescence (Fleishmann, et al., *Proceedings of the National Academy of Sciences, U.S.A.*, 81:6958, 1984), and by co-immunoprecipitation with transcribed DNA (Gilmore, et al., *Cell*, 44:401, 1986; Muller, et al., *EMBO Journal*, 1237, 1985). Furthermore, topoisomerase I cleavage sites have been mapped to regions in and around transcribed DNA (Bonner, et al., *Cell*, 41:541, 1985; Gilmour, et al., *Molecular Cell Biology*, 7:141, 1987; Stewart, et al., *Cell*, 50:109, 1987). Nonetheless, at least in yeast, topoisomerase II can apparently substitute for the functions of topoisomerase I in transcription (Uemura, et al., *EMBO Journal*, 3:1737, 1984; Thrash, et al., ibid).

Of further interest is the use of topoisomerase I in classifying autoimmune disease. Autoimmune diseases are diseases in which an animal's immune system attacks its own tissues. Often the various types of autoimmune disease can be characterized based upon the specificity of autoantibodies which are produced. For example, it is well known that the serum of patients having the connective tissue autoimmune disease progressive systemic sclerosis (PSS), also known as scleroderma, frequently contain antibodies to such nuclear antigens as topoisomerase I. Thus, the ability to accurately detect the presence of antibodies reactive with topoisomerase I can greatly assist in evaluating the prognosis and planning, or monitoring, the appropriate therapy of patients with scleroderma.

Unfortunately, the existing commercial dectection systems utilize crude exacts of cell nuclei, usually of rabbit or bovine origin, which contain antigens other than topoisomerase I. As a result, these systems will detect antibodies which react with nuclear antigens other than topoisomerase I such as, for example, the centromere, and, as a result, may give false positive results which can lead to an incorrect diagnosis. Thus, there is considerable need for a system which detects only antibodies to topoisomerase I and not other eukaryotic peptides.

SUMMARY OF THE INVENTION

It is a major object of the present invention to provide a DNA sequence which encodes eukaryotic topoisomerase I polypeptide.

Another object of the present invention is to provide a prokaryotic or eukaryotic host cell transformed or transfected with a DNA sequence which encodes eukaryotic topoisomerase I polypeptide such that the host cell can express this polypeptide.

Yet another object of the present invention is to provide a biologically functional plasmid or viral DNA vector which includes a DNA sequence encoding eukaryotic topoisomerase I polypeptide.

It is still another object of the present invention to provide a DNA sequence consisting essentially of a DNA sequence encoding a polypeptide which has an amino acid sequence possessing at least one epitope for binding topoisomerase I autoantibodies.

It is an object of the invention to provide a method of producing eukaryotic topoisomerase I polypeptide in host cells.

Another object of the present invention is to provide a method of detecting autoantibodies to eukaryotic topoisomerase I.

These and other objects are provided by one or more of the following embodiments of the present invention. In one embodiment a DNA sequence is provided which encodes eukaryotic topoisomerase I polypeptide.

In another embodiment a biologically functional plasmid or viral DNA vector is provided which includes a DNA sequence encoding for eukaryotic topoisomerase I polypeptide.

In another embodiment, a method of producing eukaryotic topoisomerase I polypeptide is presented which comprises providing a host cell which can replicate and express an intron-free DNA sequence of eukaryotic topoisomerase I polypeptide, growing the host cell, and recovering the eukaryotic topoisomerase I polypeptide. Also contemplated by the present invention are the transformed or transfected host cells themselves.

In yet another embodiment eukaryotic topoisomerase I polypeptide is provided which is substantially free of other eukaryotic non-topoisomerase I polypeptides.

In still another embodiment, a method of detecting autoantibodies to eukaryotic topoisomerase I polypeptide is provided which comprises contacting a sample with the polypeptide expressed by the DNA sequence of the invention, incubating the sample with the polypeptide for a period of time and under conditions sufficient for the autoantibodies to bind to the polypeptide, separating the autoantibodies which are bound to the polypeptide from the rest of the sample, and detecting the presence of the autoantibodies which bind to the polypeptide.

A major advantage of the present invention is that it provides the art with a ready source of eukaryotic topoisomerase I polypeptide corresponding to that purified from natural sources, while avoiding the problems associated with the isolation of naturally occurring eukaryotic topoisomerase I polypeptide to separate it from other eukaryotic non-topoisomerase I polypeptides. This absence of other eukaryotic non-topoisomerase I polypeptides is significant in that it allows the development of test systems which will only detect antibodies specifically reactive with topoisomerase I polypeptides.

Another advantage of providing eukaryotic topoisomerase I polypeptide in host cells is that by so doing it is possible to obtain much larger quantities of the polypeptide than are currently practicably available from natural sources. As a consequence, not only is it possible to use the polypeptide of the invention to more accurately classify patients with such autoimmune rheumatic diseases as scleroderma, but it is also now possible to also provide commercially useful quantities of topoisomerase I polypeptide for use in diagnostic systems.

The eukaryotic topoisomerase I polypeptides of the present invention retain the ability to bind autoantibodies to eukaryotic topoisomerase I even though the prokaryotic host in which the polypeptides of the invention can be cloned degrades the transcribed topoisomerase I molecules into a spectrum of polypeptides.

DESCRIPTION OF THE DRAWINGS

FIG. 1. Restriction map and strategy for sequencing topoisomerase I cDNA clones T1A and T1B. The bold lines represent the cDNA coding sequences and the thin lines the presumptive 5' and 3' untranslated regions. A partial restriction endonuclease map is shown (X, Xho I; M, Xmn I; N, Nde I; H, Hind III; R, Eco RV; E, Eco RI). The arrows represent the individual subclones that were sequenced to determine the complete cDNA sequence. The subclone indicated by the asterisk was used to probe the DNA blot shown in FIG. 4.

FIG. 2. Expression of fp-topo I and comparison of the proteolysis maps of human nuclear topoisomerase I and fp-topo I. 2A) Immunoblots of lysates of bacteria harboring pATH11(−) or pATH11-TIA(F) probed with anti-topoisomerase I serum. 2B) Proteolysis maps. Human topoisomerase I (T) and fp-topo I (F) obtained by excision from NaDodSO₄ polyacrylamide gel. Lanes labeled "—" were loaded with gel slices (between 95 and 116kDa) excised from SDS-PAGE gels loaded with bacterial lysates that contained the pATH11 expression vector without the T1A cDNA. V8 protease or chymotrypsin were overlaid so that proteolysis could proceed during subsequent electrophoresis. An immunoblot probed with anti-topoisomerase I autoimmune serum is shown. Molecular weight markers: 200, 116, 95, 68, 60, 48, 40, 29, 18.4, 16.9 kDa.

FIG. 3. 3A) Topoisomerase I activity in lysates of bacteria harboring pATH11 or pATH11-T1A. Lysates of bacteria harboring pATH11 (−) or pATH11-T1A(+) were added to reaction mixtures containing either buffer P (with free $Mg^{++}$) or buffer E (without free $Mg^{++}$). 3B) Immunodepletion of $Mg^{++}$-independent topoisomerase I activity from bacterial lysates. Lysates of bacteria harboring pATH11-T1A were immunoprecipitated with either normal human (NH) or with anti-topoisomerase I (alpha-topo) serum. The supernatant (lane 1) and serial two-fold dilutions (lanes 2 and 3) were then assayed for topoisomerase I activity in the absence of free $Mg^{++}$.

FIG. 4. Human topoisomerase I as encoded by a 4.1 kb mRNA transcribed from a single copy human gene. 4A) Human genomic DNA cut with EcoR I (R) or Hind III (H) was probed with the fragment from T1A which extends from codon 484 to 578 (fragment with asterisk in FIG. 1, also see FIG. 6). DNA size markers: 23130, 9416, 6557, 4361, 2322, 2027, 1353 bp. 4B) Polyadenylated mRNA from HeLa cells probed with the entirety of T1A. RNA markers: 9490, 7460, 4400, 2370, 1350 nucleotides.

FIG. 5A-5C. Sequence of topoisomerase I cDNA. The sequence was performed according to the strategy outlined in FIG. 1. The sequence includes the presumptive 5' and 3' untranslated sequences of 211 and 1139 bases, respectively.

FIG. 6. Comparison of the amino acid sequences of human (bottom) and Saccharomyces cerevisiae (top) topoisomerase I as deduced from their DNA sequences. 6A) Double dots represent amino acid identities between S. cerevisiae and human type I topoisomerases. Single dots represent similarity in sequence due to conservative changes. Asterisks denote a large gap placed in the human sequence in order to maintain maximal alignment. 6B) Schematic diagram of regions of greatest similarity between human and S. cerevisiae amino acid sequences. Thin lines represent regions without apparent similarity while the heavy bars represent regions of significant similarity. Regions shown as heavy bars show 55% identity or 69% similarity when conservative changes are considered.

DETAILED DESCRIPTION

The present invention relates to the manipulation of genetic materials by recombinant procedures which make possible the production of polypeptides possessing part or all of the primary structural conformation for one or more of the epitopes for binding autoantibodies to eukaryotic topoisomerase I. These polypeptides are highly useful for the immunological detection of autoantibodies reactive with them since such autoantibodies are indicative of autoimmune rheumatic diseases.

The cDNA clones produced by the present invention encode human topoisomerase I is demonstrated by the fact that: (1) partial proteolysis maps of the cloned fusion protein and naturally-occurring nuclear topoisomerase I are virtually identical; (2) the 67,700 Dalton carboxy-terminal portion of the cloned protein exhibits topoisomerase I activity in vitro; and (3) the cloned cDNA shows a high degree of sequence similarity with topoisomerase I from yeast (Thrash, et al., ibid). The hybridization data obtained indicate that human cells contain only a single locus complementary to this cDNA and that this locus gives rise to a single mRNA.

Figure 6A:
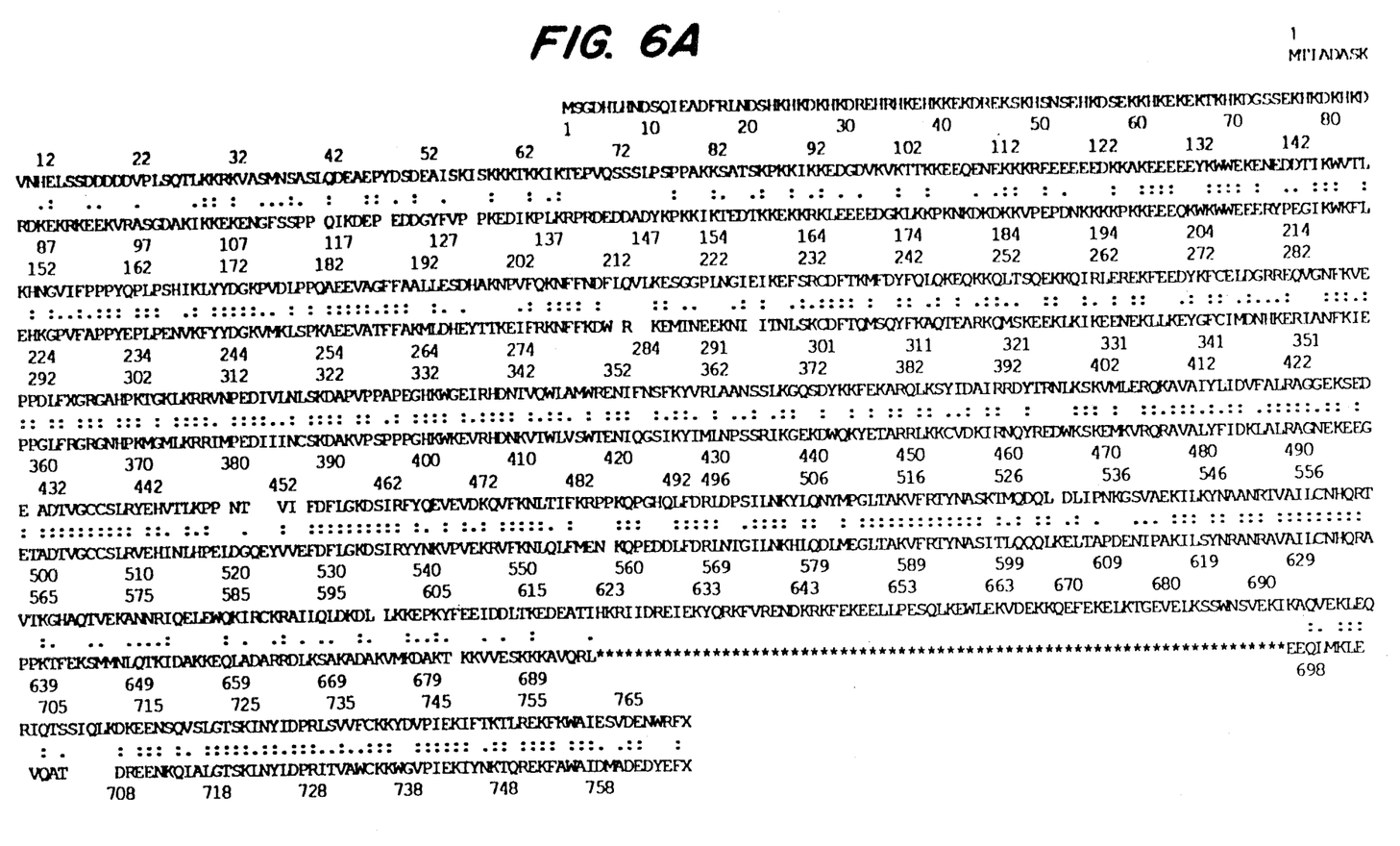
Figure 6B:
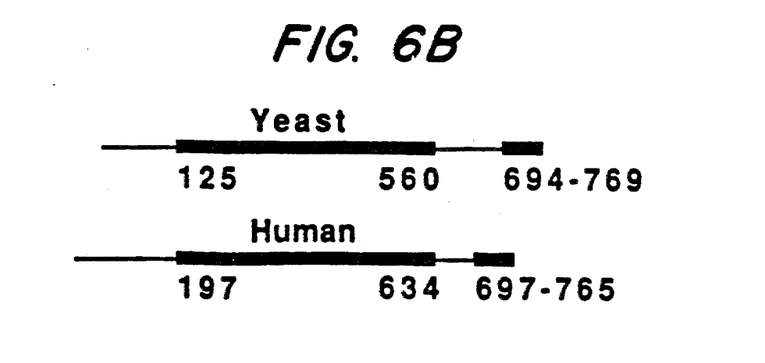

Topoisomerase I shows a significant degree of evolutionary amino acid sequence conservation (42%) between man and yeast. A comparison of the polypeptide sequences of human and yeast enzymes (FIG. 6A) reveals two regions of relatively stronger sequence similarity which are designated region I (435 residues, starting at 197 in the humans) and region II (the carboxy-terminal 70 residues). At optimal alignment both enzymes share a 54% amino acid sequence identity which increases to 69% when conservative substitutions are included. A schematic which indicates the relative locations and extent of regions I and II is shown in FIG. 6B.

Interestingly, human and yeast topoisomerase I are predicted to be nearly the same molecular weight, despite the presence of approximately 70 additional residues in the yeast sequence between regions I and II. These additional sequences in the yeast enzyme are balanced by the fact that in the human sequence 70 additional residues are present at the amino terminus.

The amino terminal region of the human protein is remarkable for its sequence composition wherein 65% of the residues are charged based on the fact that of the 197 residues present in the non-similar region between yeast and human, 80 are basic and 48 are acidic. Remarkably, the entire protein has 43% charged residues overall.

The cloned human topoisomerase I was found to have no significant sequence similarities with *E. coli* type I topoisomerase I. Although it has been previously shown that topoisomerase I from yeast and *E. coli* share a small region of sequence similarity, this region was not found in the human sequence for topoisomerase I.

Studies on the topoisomerase I of the invention clearly indicate that the catalytic site is present in the carboxy-terminal 68 kDa region of the polypeptide. The highly charged amino terminal portion of the polypeptide may modulate the activity of the catalytic moiety or, alternatively, be involved in protein-protein interactions. Possible targets for such interactions include regulatory proteins, components of the transcriptional apparatus, or perhaps histones.

In the present invention cDNA clones encoding human topoisomerase I were obtained from a library of human placental mRNA using the lambda gt 11 expression method (Young, et al., *Science*, 222:778, 1983). Clones expressing human topoisomerase I were screened by immuno-probing with an anti-topoisomerase I autoimmune serum.

The development of specific DNA sequences encoding topoisomerase I polypeptide for splicing into DNA vectors can be accomplished using a variety of techniques. For example, alternative methods which can be employed include: (1) the isolation of a doublestranded DNA sequence from the genomic DNA of the eukaryote; (2) the chemical manufacture of a DNA sequence to provide the necessary codons for the polypeptide of interest; and (3) the in vitro synthesis of a doublestranded DNA sequence by reverse transcription of mRNA isolated from a eukaryotic donor cell. In the latter case, a DNA complement of mRNA is formed which is generally referred to as cDNA.

The manufacture of DNA sequences is frequently the method of choice when the entire sequence of amino acid residues of the desired polypeptide product is known. When the entire sequence of amino acid residues of the desired polypeptide is not known, the direct manufacture of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells which have a high level of genetic expression. In those cases where significant portions of the polypeptide's amino acid sequence are known, the production of labeled single stranded DNA probe sequences duplicating a sequence putatively present in the target cDNA may be employed in DNA/DNA hybridization procedures which are carried out on cloned copies of the cDNA which have been denatured into a single stranded form (Jaye, et al., *Nucleic Acid Research*, 11:2325, 1983).

Hybridization procedures are useful for the screening of recombinant clones by using labeled mixed synthetic oligonucleotide probes wherein each is potentially the complete complement of a specific DNA sequence in the hybridization sample which includes a heterogeneous mixture of single stranded DNAs or RNAs. These procedures are particularly useful in the detection of cDNA clones derived from sources where extremely low amount of mRNA sequences relating to the polypeptide of interest are present. In other words, by using stringent hybridization conditions directed toward avoidance of non-specific binding it is possible, for example, to allow the autoradiographic visualization of a specific cDNA clone by the hybridization of the target DNA to that single probe in the mixure which is its complete complement (Wallace, et al., *Nucleic Acid Research*, 9:879, 1981).

Of the three above-noted methods for developing specific DNA sequences for use in recombinant procedures the use of genomic DNA isolates is the least common. This is especially true when it is desirable to obtain the microbial expression of mammalian polypeptides.

The present invention provides novel polypeptides of eukaryotic topoisomerase I which have part or all of the primary structural confirmation, that is, a continuous sequence of amino acid residues, having at least one epitope for autoantibodies to eukaryotic topoisomerase I.

When the eukaryotic topoisomerase I encoded by the DNA sequence of the invention is expressed in a prokaryotic host it is almost immediately degraded into a spectrum of polypeptide fragments. As a consequence, it was surprising the find that these polypeptide fragments retain at least one epitope capable of reacting with autoantibodies to eukaryotic topoisomerase I. Thus, it is possible to use the polypeptide fragments of the invention rather than intact eukaryotic topoisomerase I to detect autoantibodies to eukaryotic topoisomerase I.

The term "polypeptide," as applied to eukaryotic topoisomerase I polypeptide, denotes any sequence of amino acids having an epitope for autoantibodies to eukaryotic topoisomerase I, wherein the sequence of amino acids is encoded by all or part of the cDNA sequences of the invention.

The polypeptides resulting from microbial expression of the DNA sequences of the invention can be further characterized by their freedom from association with other human polypeptides or other contaminants which might otherwise be associated with eukaryotic topoisomerase I in its natural cellular environment or in such extracellular fluids as plasma or urine.

The term "host" is meant to include not only prokaryotes, but also such eukaryotes as yeast, filamentous fungi, as well as plant and animal cells which can replicate and express an intron-free DNA sequence of eukaryotic topoisomerase I. However, prokaryotes are preferred as the host organism.

The term "prokaryotes" is meant to include all bacteria which can be transformed or transfected with the eukaryotic gene for the expression of eukaryotic topoisomerase I. Procaryotic hosts may include gram negative as well as gram positive bacteria such as, for example, *E. coli, S. typhimurium, Serratia marcescens* and *Bacillus subtilis.*

A recombinant DNA molecule coding for the eukaryotic topoisomerase I polypeptides can be used to transform or transfect the host using any of the techniques commonly known to those of ordinary skill in the art. Especially preferred is the use of a plasmid or a virus containing the eukaryotic topoisomerase I coding sequence for purposes of prokaryotic transformation or transfection, respectively.

Methods for preparing fused, operably linked genes and expressing them in bacteria are well-known in the art (Maniatis, et al., *Molecular Cloning: A Laboratory Manual*, Cold Spring Harbor Laboratory, Cold Spring Harbor, N.Y., 1981). The genetic constructs and methods described therein can be utilized for expression of eukaryotic topoisomerase I in prokaryotic hosts.

In general, expression vectors containing promoter sequences which facilitate the efficient transcription of the inserted eukaryotic genetic sequence are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The polypeptides of the invention can then be isolated from the growth medium, cellular lysates, or cellular membrane fractions.

The isolation and purification of the microbially expressed polypeptides of the invention may be by any conventional means such as, for example, preparative chromatographic separations and immunological separations such as those involving the use of monoclonal or polyclonal antibody.

By having provided the sequence of amino acid residues of eukaryotic topoisomerase I, the present invention provides for the manufacture of DNA sequences which code for the host expression of polypeptide analogs or derivatives of eukaryotic topoisomerase I which differ from naturally-occurring forms in terms of the identity or location of one or more amino acid residues and which share some or all of the epitopes of naturally-occurring polypeptide forms.

Figure 5A:
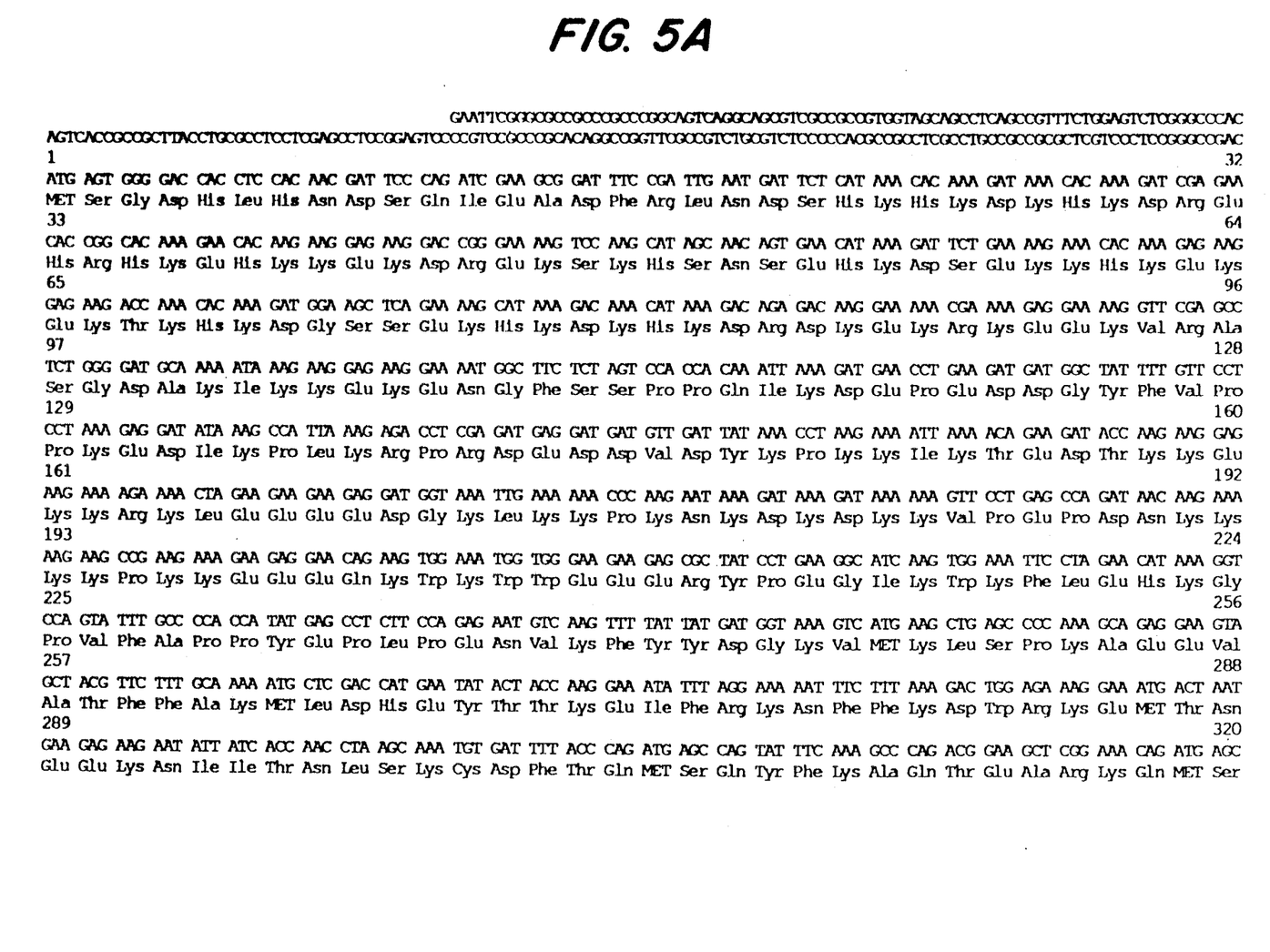

The novel DNA sequences of the invention include all sequences useful in providing the expression in prokaryotic or eukaryotic host cells of polypeptides which have at least a part of the primary structural confirmation for one or more epitopes capable of reacting with autoantibodies to eukaryotic topoisomerase I which are comprehended by: (a) the DNA sequence as set forth in FIG. 5 or its complementary strand; (b) DNA sequences which hybridize to DNA sequences defined in (a) or fragments thereof; and (c) DNA sequences which, but for the degeneracy of the genetic code, would hybridize to DNA sequences defined in (a) and (b) above. Specifically comprehended in (b) are genomic DNA sequences which encode allelic variant forms of eukaryotic topoisomerase I. Part (c) specifically comprehends the manufacture of DNA sequences which encode eukaryotic topoisomerase I, eukaryotic topoisomerase I fragments and eukaryotic topoisomerase I analogs wherein the DNA sequences thereof may incorporate codons which facilitate translation of mRNA in non-vertebrate hosts.

Since the cDNA sequence of the invention encodes essentially the entire human topoisomerase I molecule it is now a matter of routine to prepare, subclone and express smaller polypeptide fragments of cDNA from this or a corresponding cDNA sequence which would encode as few as one epitope for autoantibodies to human topoisomerase I. The presence of such an epitope on a cloned polypeptide can then be confirmed using, for example, sera from a patient with autoantibodies to topoisomerase I.

The eukaryotic topoisomerase I of the invention is particularly suited for use in immunoassays in which it can be utilized in liquid phase or bound to a solid phase carrier. In addition, the eukaryotic topoisomerase I used in these assays can be detectably labeled in various ways.

Examples of immunoassays which can utilize eukaryotic topoisomerase I of the invention are competitive and non-competitive immunoassays in either a direct or indirect format. Examples of such immunoassays are the radioimmunoassay (RIA) the sandwich (immunometric) assay and the Western blot assay. Detection of antibodies which bind to the eukaryotic topoisomerase I of the invention can be done utilizing immunoassays which run in either the forward, reverse, or simultaneous modes, including immunohistochemical assays on physiological samples. The concentration of eukaryotic topoisomerase I which is used will vary depending on the type of immunoassay and nature of the detectable label which is used. However, regardless of the type of immunoassay which is used, the concentration of eukaryotic topoisomerase I utilized can be readily determined by one of ordinary skill in the art using routine experimentation.

The eukaryotic topoisomerase I of the invention can be bound to many different carriers and used to detect the presence of antibody specifically reactive with the polypeptide. Examples of well-known carriers include glass, polystyrene, polyvinyl chloride, polypropylene, polyethylene, polycarbonate, dextran, nylon, amylases, natural and modified celluloses, polyacrylamides, agaroses and magnetite. The nature of the carrier can be either soluble in insoluble for purposes of the invention. Those skilled in the art will know of other suitable carriers for binding eukaryotic topoisomerase I, or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, the antibody which binds to eukaryotic topoisomerase I of the invention may be present in various biological fluids and tissues. Any sample containing a detectable amount of antibodies to eukaryotic topoisomerase I can be used. Normally, a sample is a liquid such as urine, saliva, cerebrospinal fluid, blood, serum and the like, or a solid or semi-solid such as tissue, feces and the like.

The above disclosure generally describes the present invention. A more complete understanding can be obtained by reference to the following specific examples which are provided herein for purposes of illustration only and are not intended to limit the scope of the invention.

EXAMPLE 1

CLONING AND EXPRESSION OF TOPOISOMERASE I

A. Recombinant DNA Procedures.

cDNA clones were obtained using the lambda gt11 expression method of Young and Davis (*Science*, 222:778, 1983). $1 \times 10^6$ recombinant phage (lambda gt11 library of human placental polyadenosine mRNA; Clontech) were plated and screened by immunoprobing with an autoimmune anti-topoisomerase I serum (Shero, et al., *Science*, 231:737, 1986), using standard methods (Maniatis, et al., ibid). DNA and RNA hybridizations were performed according to standard procedures (Maniatis, et al., ibid). Blots were hybridized at 42° C. in the presence of 50% formamide and washed at 50° C. with a solution of 15 mM NaCl, 1.5 mM Na citrate and 0.1% NaDodSo$_4$ (Maniatis, et al., ibid). cDNA sequences were determined by constructing an exonuclease III deletion series of clone T1A as described by Henicoff (*Gene*, 28:351, 1984). The deleted fragments were subcloned into M13 for sequencing by the dideoxynucleotide chain termination method (Sanger, et al., *Proceedings of the National Academy of Sciences, U.S.A.*, 74:5463, 1977). Other sequences were determined by cloning specific restriction fragments into M13.

B. Expression of Topoisomerase I as a Fusion Protein in Bacteria.

The cloned cDNA T1A (see FIG. 1) inserted into the pATH11 expression vector (provided by T. J. Koerner, Duke University) was expressed in *E. coli* (DH1) as a fusion protein comprised of 32kDa of the bacterial trpE protein linked to 67.7 kDa of the protein encoded by the cDNA, as previously described (Earnshaw, et al., *Journal of Cell Biology*, 104, 817, 1987). This fusion protein (fp-topo I) was induced and visualized by immunoblotting as described (Earnshaw, et al., ibid). All immunoblotting was done with the same anti-topoisomerase I autoimmune serum.

$1 \times 10^6$ recombinant phage were screened with topoisomerase I antiserum (Shero, et al., ibid). Eight immunoreactive plaques were purified and the longest cDNA clone (T1A, 2929 bp) was analyzed by restriction mapping and sequenced according to the strategy outlined in FIG. 1. Longer cDNAs were obtained by screening additional recombinant phage with the 5' Eco RI-Nde I fragment of T1A as a hybridization probe. 10 additional clones were obtained including clone T1B (3645 bp, FIG. 1), which appears to contain the entire coding region (see below). Both T1A and T1B terminate at their 5' ends with an Eco RI site (located in the 3' non-translated region) which was also found in several other clones obtained from both the antibody and DNA hybridization screens.

Figure 2A:
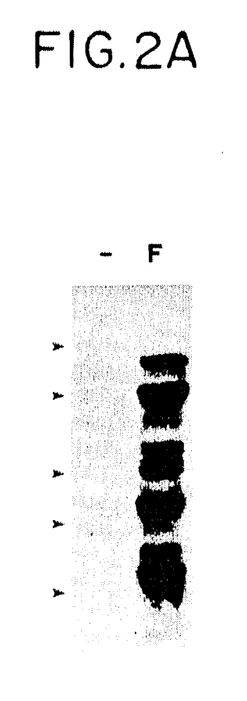

Clone T1A was subcloned into a bacterial expression plasmid (pATH11, in Earnshaw, et al., ibid) in which protein encoded by the cDNA is linked in a fusion protein to the 32 kDa amino terminal portion of the bacterial trpE protein. Bacterial lysates harboring pATH11 containing T1A (pATH11-T1A) contained several immunoreactive polypeptides (probably proteolysis fragments) that were not evident in lysates harboring only pATH11 (FIG. 2A).

EXAMPLE 2

CHARACTERIZATION OF CLONED TOPOISOMERASE I

A. Proteolysis Mapping.

Proteolysis maps of human topoisomerase I and fp-topo I were performed as described (Cleveland, *Methods in Enzymology*, 96:222, 1983), except that immunoblotting was used to visualize the proteolysis fragments instead of Coomassie blue staining. Gel bands corresponding to human topoisomerase I and fp-topo I (the largest two bands) were excised in small strips, inserted into the wells of another NaDodSO$_4$ gel, and overlaid with either chymotrypsin (100 g) or V8 protease from *Staphylococcus aureus* (1.0 or 10.0 g). Electrophoresis was initiated at 50 volts until the dye completely entered the stacker. Proteolysis occurs as the proteins stack (Cleveland, ibid).

Figure 2B:
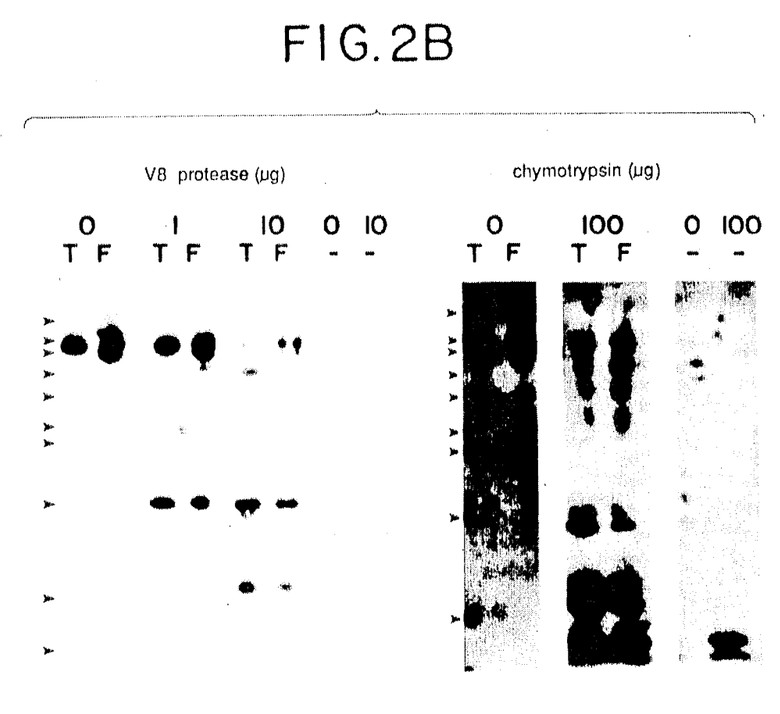

To examine the biochemical similarity between the fusion protein (fp-topo I) and human nuclear topoisomerase I, their proteolysis maps were compared. HeLa nuclear topoisomerase I and fp-topo I (the largest two species seen in FIG. 2A) were obtained by excision from NaDodSO$_4$ polyacrylamide gels. Human nuclear topoisomerase I and fp-topo I gave rise to nearly identical patterns of immunoreactive proteolytic fragments, indicating that the two polypeptides are closely related (FIG. 2B). The virtual identity of these proteolysis maps indicates that the immunoreactive proteolysis fragments of fp-topo I contain nondetectable amounts of trpE.

B. DNA Topoisomerase I Assays.

Assays for bacterial and human topoisomerase I were performed essentially as described by Thrash et al. (ibid).

Figure 3A:
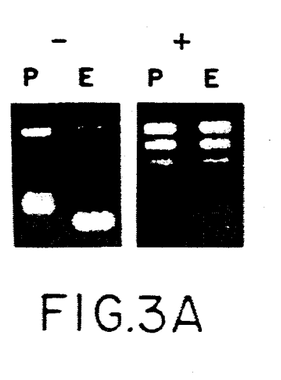

To confirm that clone T1A encoded topoisomerase I, fp-topo I was assayed for Mg$^{++}$-independent supercoil-relaxing activity, a characteristic of eukaryotic topoisomerase I (Thrash, et al., ibid). Bacteria expressing fp-topo I (lanes +), and nonexpressing control bacteria (harboring pATH11 only, lanes −) were lysed, and after pelleting debris, aliquots of the supernatants were tested for their ability to relax super coiled DNA (FIG. 3A). In buffer P which contains excess Mg$^{++}$, lysates of bacteria that were not expressing fp-topo I contained supercoil-relaxing activity due to bacterial topoisomerase I, which requires Mg$^{++}$ as a cofactor (−, lane P). In buffer E, which does not contain free Mg$^{++}$, bacterial topoisomerase I activity is abolished (−, lane E). In lysates of bacteria expressing fp-topo I, supercoil-relaxing activity is evident both in the presence and absence of free Mg$^{++}$ (+, lanes P and E). This Mg$^{++}$-independent activity, characteristic of eukaryotic type I topoisomerases, must be due to fp-topo I. The difference in the distribution of topoisomers produced by bacterial and human type I topoisomerases is characteristic of the enzymes (Thrash, et al., ibid).

Figure 3B:
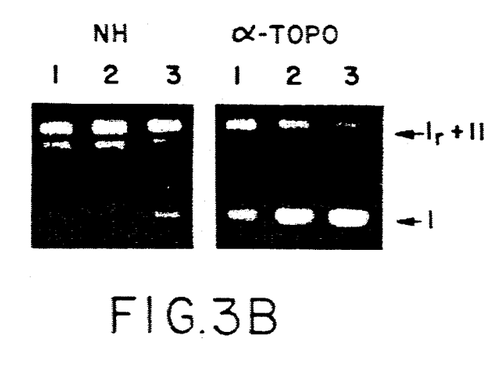

To demonstrate further that fp-topo I encodes human topoisomerase I, lysates of bacteria expressing fp-topo I were immunoprecipitated with anti-topoisomerase I autoimmune serum. Mg$^{++}$-independent topoisomerase I activity was removed from these lysates, but not from control lysates treated with normal human serum (FIG. 3B). This data shows that T1A encodes a catalytically active portion of human topoisomerase I.

Figure 4A:
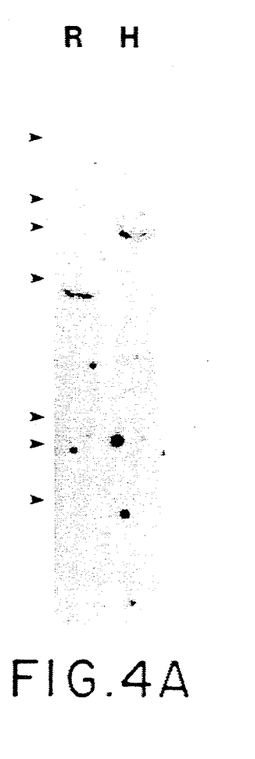

To investigate whether topoisomerase I is encoded by a single gene or a family of genes as has been seen for many other eukaryotic proteins such as tubulins (Cleveland, et al., *Annual Review of Biochemistry*, 54:331, 1985), blots of human genomic DNA that had been digested with either Eco R1 or Hind III were analyzed. A DNA segment spanning codons 484 to 578 (fragment with asterisk in FIG. 1, and see FIG. 6A) was prepared from T1A and used as a hybridization probe. The resultant autoradiograph is shown in FIG. 4A. Only a single DNA fragment was detected in either digest. Since moderate conditions of stringency were utilized, only a single locus highly homologous to the cloned topoisomerase I sequence is apparently present in the human genome.

Figure 4B:
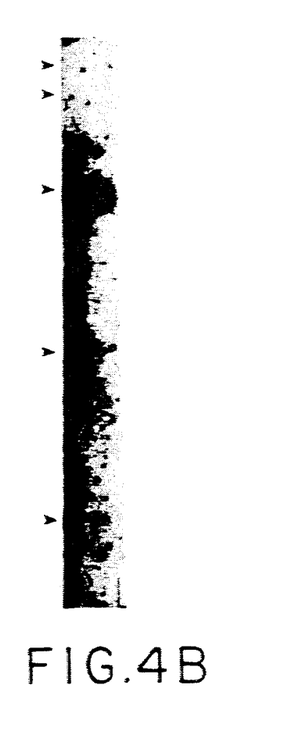

To determine the size of the mRNA that encodes human topoisomerase I, we probed blots of HeLa cell poly(A) RNA with the entirety of T1A. A single RNA species (FIG. 4B) of 4100 nucleotides was detected.

C. The Deduced Amino Acid Sequence of Human Topoisomerase I.

Figure 1:
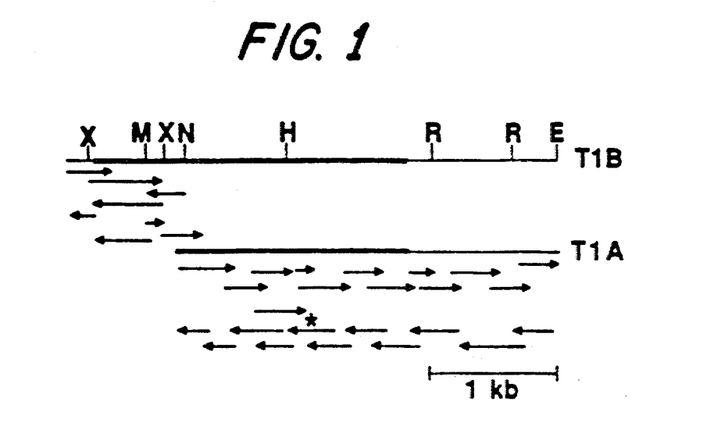

The nucleotide sequence of the human topoisomerase I cDNA contained in clones T1A and T1B was determined according to the strategy shown in FIG. 1. The 3645 base T1B sequence begins with a putative 5' untranslated region of 211 nucleotides, followed by a 765 amino acid open reading frame, and terminates with 1139 nucleotides of 3' untranslated sequence. The encoded polypeptide has a molecular weight of 90,649 Da and a calculated isoelectric point of 10.05 (26% basic and 18% acidic residues). The deduced molecular weight is somewhat smaller than the 100,000 Da estimate for authentic topoisomerase I determined by NaDodSO$_4$-PAGE(Liu, et al., *Proceedings of the National Academy of Sciences, U.S.A.*, 78:3487, 1981), however, apparent molecular weights may differ substantially from actual molecular weights (Earnshaw, et al., ibid).

Since the corresponding mRNA is 4100 bases in length, it is estimated that clone T1B is 250–350 amino acids short of full length assuming a poly(A) tail of 100–200. The missing sequence may be either 5' or 3' to the open reading frame. Since the 3' end of the clones is bounded by a natural Eco RI site, the true length of the 3' nontranslated region is unknown.

It is not known whether the cDNA sequence presented in FIG. 5 represents the entire protein coding region. Although the unambiguous identification of initiation methionines from cDNA sequences is problematic, the specified initiator codon appears to be correct for three reasons. 1) The first AUG in the clone is in frame with a translation unit that encodes a protein of approximately the same size as authentic human topoisomerase I. 2) This AUG codon is immediately preceded by nucleotides that have been associated with eukaryotic start codons (Kozak, *Cell*, 44:283, 1986): a purine is in position -3, and cytosines are in positions -1, -4 and -5. 3) The 211 bp sequence upstream of the putative start codon is 73% GC rich and is not deficient in CpG (the 211 bp sequence downstream of the putative start codon is only 40% GC rich). Such a sequence arrangement is characteristic of the 5' ends of many genes that do not display tissue specific expression (Bird, *Nature*, 321:209, 1986). Despite this, it should be noted that an open reading frame extends from the presumptive initiation codon all the way to the 5' end of the clone.

EXAMPLE 3

DETECTION OF AUTOANTIBODIES TO TOPOISOMERASE I IN CLINICAL SPECIMENS

Sera from normal individuals and from thirteen patients suspected of having autoantibodies to human topoisomerase I were tested using the Western blot technique (Earnshaw, et al., *Journal of Clinical Investigation*, 72:425, 1986) and the polypeptides expressed by the cDNA sequence of the invention. The thirteen sera from patients suspected of having autoantibodies to human topoisomerase I had previously shown a positive reaction for the presence of such autoantiodies when tested in a commercially available diagnostic test which utilizes a crude extract from mammalian nuclei. When these same thirteen sera were tested against the polypeptides of the invention only eleven of the patient's sera were positive. Since the Western technique is more sensitive than the technique utilized in the commercial test, two of these patients may have been false positive. Since the commercial test contains other nuclear antigens in addition to topoisomerase I such as, for example, the centromere, these patients sera may have reacted to one or more of these other non-to-poisomerase I antigens in the commercial test. None of the normal sera which were tested reacted with the polypeptides of the invention.

The invention now being fully described, it will be apparent to one of ordinary skill in the art that many changes and modifications can be made thereto without departing form the spirit or scope of the invention.

We claim:

1. A cDNA sequence consisting essentially of a cDNA sequence encoding human topoisomerase I.

2. A host cell transformed or transfected with the cDNA sequence of claim 1.

3. A biologically functional plasmid or viral DNA vector including the cDNA sequence of claim 1.

4. A host cell stably transformed or transfected with a DNA vector according to claim 3.

5. A cDNA sequence consisting essentially of a cDNA sequence encoding a polypeptide having an amino acid sequence possessing at least one epitope for autoantibodies to human topoisomerase I.

Figure 5C:
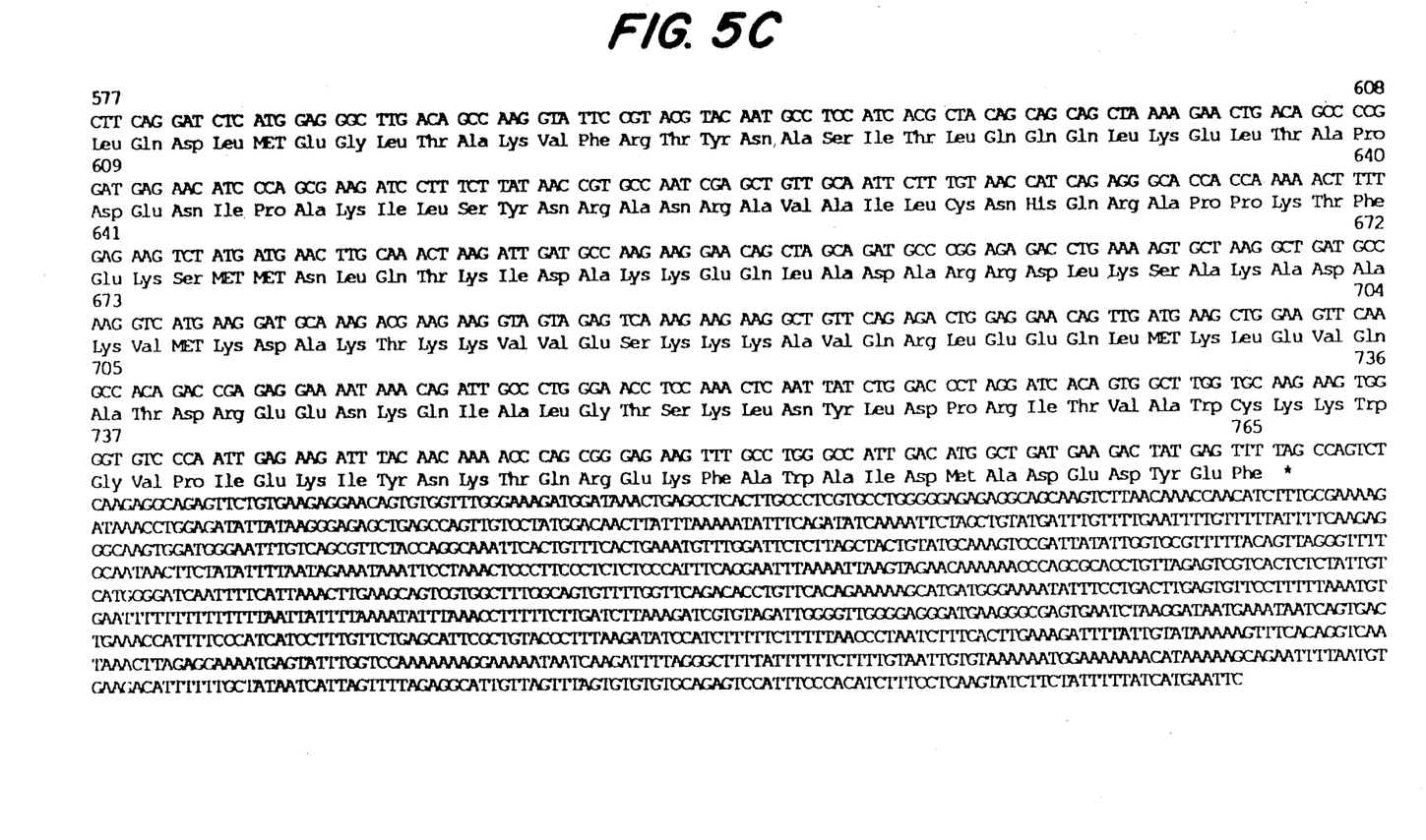

6. The cDNA sequence according to claim 5 and including the protein coding region set forth in FIG. 5.

7. The cDNA sequence of claim 5, wherein said cDNA sequence codes for the expression of human topoisomerase I.

8. A host cell transformed or transfected with the cDNA sequence of claim 5.

9. A method of providing eukaryotic topoisomerase I polypeptide having at least one epitope for autoantibodies to eukaryotic topoisomerase I comprising:
   (a) providing a host cell which replicates and expresses an intron-free DNA sequence of human topoisomerase I polypeptide;
   (b) growing said host cell; and
   (c) recovering said human topoisomerase I polypeptide.

10. The method of claim 9, wherein said eukaryotic topoisomerase I is human topoisomerase I.

11. A method of detecting autoantibodies to eukaryotic topoisomerase I which comprises:
   (a) contacting a sample containing serum with a polypeptide encoded by the cDNA sequence of claim 1, said polypeptide being free of other human polypeptides;

(b) incubating the components of step (a) for a period of time and under conditions sufficient for said autoantibodies to bind to said polypeptide;

(c) separating said autoantibodies bound to said polypeptide from said sample; and (d) detecting the presence of said autoantibodies to said polypeptide.

12. The method of claim 11 wherein said eukaryotic topoisomerase I is human topoisomerase I.

13. The method of claim 11 wherein said sample is from a human.

14. The method of claim 11 wherein said detecting utilizes a detectably labeled protein capable of binding to said autoantibody.

15. The method of claim 14 wherein said binding protein is a detectably labeled second antibody.

16. The method of claim 15 wherein said detectable label is selected from the group consisting of a radioisotope, a fluorescent compound, a colloidal metal, a chemiluminescent compound, a bioluminescent compound and an enzyme.

* * * * *